(12) United States Patent
Shin et al.

(10) Patent No.: US 10,344,044 B2
(45) Date of Patent: Jul. 9, 2019

(54) LIGAND COMPOUND, CATALYST SYSTEM FOR OLIGOMERIZATION, AND METHOD FOR OLEFIN OLIGOMERIZATION USING THE SAME

(71) Applicant: LG CHEM, LTD., Seoul (KR)

(72) Inventors: Eun Ji Shin, Daejeon (KR); Yong Ho Lee, Daejeon (KR); Jin Young Park, Daejeon (KR); Seok Pil Sa, Daejeon (KR); Ki Soo Lee, Daejeon (KR); Seul Ki Im, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/542,829

(22) PCT Filed: Jan. 26, 2016

(86) PCT No.: PCT/KR2016/000823
§ 371 (c)(1),
(2) Date: Jul. 11, 2017

(87) PCT Pub. No.: WO2016/167455
PCT Pub. Date: Oct. 20, 2016

(65) Prior Publication Data
US 2017/0369515 A1    Dec. 28, 2017

(30) Foreign Application Priority Data

Apr. 15, 2015 (KR) .................. 10-2015-0053169
Jan. 25, 2016 (KR) .................. 10-2016-0008490

(51) Int. Cl.
| | | |
|---|---|---|
| C07C 2/32 | (2006.01) | |
| C07F 9/50 | (2006.01) | |
| C08F 4/69 | (2006.01) | |
| B01J 31/14 | (2006.01) | |
| B01J 31/18 | (2006.01) | |
| C07C 11/02 | (2006.01) | |
| C07F 11/00 | (2006.01) | |
| C08F 10/02 | (2006.01) | |
| C07C 11/107 | (2006.01) | |
| C07F 9/46 | (2006.01) | |

(52) U.S. Cl.
CPC .......... *C07F 9/5027* (2013.01); *B01J 31/143* (2013.01); *B01J 31/189* (2013.01); *C07C 2/32* (2013.01); *C07F 9/46* (2013.01); *C07F 11/00* (2013.01); *C07F 11/005* (2013.01); *B01J 2231/20* (2013.01); *B01J 2531/62* (2013.01); *C07C 2531/14* (2013.01); *C07C 2531/18* (2013.01); *C07C 2531/24* (2013.01)

(58) Field of Classification Search
CPC combination set(s) only.
See application file for complete search history.

(56) References Cited

U.S. PATENT DOCUMENTS

| | | | |
|---|---|---|---|
| 7,964,763 B2 | 6/2011 | Dixon et al. | |
| 8,076,523 B2 | 12/2011 | Bollmann et al. | |
| 2005/0119516 A1 | 6/2005 | Dixon et al. | |
| 2006/0229480 A1 | 10/2006 | Blann et al. | |
| 2011/0046429 A1 | 2/2011 | Aliyev et al. | |
| 2012/0172645 A1* | 7/2012 | Sydora ................ | B01J 31/143 585/511 |
| 2013/0296518 A1 | 11/2013 | Sato et al. | |

FOREIGN PATENT DOCUMENTS

| | | |
|---|---|---|
| JP | 2005-513115 A | 5/2005 |
| JP | 2006-517528 A | 7/2006 |
| JP | 2009-120588 A | 6/2009 |
| KR | 10-2010-0113534 A | 10/2010 |
| WO | 03/053891 A1 | 7/2003 |
| WO | 2005/123633 A1 | 12/2005 |

OTHER PUBLICATIONS

Tao Jiang et al., "The effect of N-aryl bisphosphineamine ligands on the selective ethylene tetramerization", Journal of Molecular Catalysis A: Chemical, vol. 279, 2008, pp. 90-93.
Esna Killian et al., "The use of bis(diphenylphosphino)amines with N-aryl functionalities in selective ethylene tri- and tetramerisation", Journal of Molecular Catalysis A: Chemical, vol. 270, 2007, pp. 214-218.
Anthea Carter et al., "High activity ethylene trimerisation catalysts based on diphosphine ligands", Chem. Commun., 2002, pp. 858-859.

* cited by examiner

*Primary Examiner* — In Suk C Bullock
*Assistant Examiner* — Ali Z Fadhel
(74) *Attorney, Agent, or Firm* — Dentons US LLP

(57) ABSTRACT

The present disclosure relates to a ligand compound, a catalyst system for oligomerization, and a method for olefin oligomerization using the same. The catalyst system for oligomerization using the ligand compound according to the present disclosure has excellent catalytic activity, exhibits high selectivity to 1-hexene and 1-octene, and greatly reduces the production of the by-products, thereby enabling efficient preparation of alpha-olefin.

12 Claims, No Drawings

LIGAND COMPOUND, CATALYST SYSTEM FOR OLIGOMERIZATION, AND METHOD FOR OLEFIN OLIGOMERIZATION USING THE SAME

CROSS REFERENCE TO RELATED APPLICATIONS

This application is a National Stage Application of International Application No. PCT/KR2016/000823 filed on Jan. 26, 2016, which claims the benefit of Korean Patent Application No. 10-2015-0053169 filed on Apr. 15, 2015 and Korean Patent Application No. 10-2016-0008490 filed on Jan. 25, 2016, all of which are hereby incorporated by reference in their entirety for all purposes as if fully set forth herein.

TECHNICAL FIELD

The present disclosure relates to a ligand compound, a catalyst system for olefin oligomerization, and a method for olefin oligomerization using the same.

BACKGROUND

Linear alpha-olefins, which are important materials used as comonomers, cleaners, lubricants, plasticizers and the like, are commercially widely used, and particularly, 1-hexene and 1-octene are used a lot as comonomers for controlling the density of polyethylene when preparing linear low-density polyethylene (LLDPE).

In the existing preparation process of LLDPE, ethylene is copolymerized with alpha-olefin comononers such as 1-hexene and 1-octene, so as to form branches in the polymer backbone to control the density.

Thus, there is a problem in that the cost of comonomers occupies a large part of production cost in the preparation of LLPDE having high comonomer content. There have been various attempts to solve the problem.

And, since alpha-olefins have various different application fields or a market sizes according to the kind, a technology of selectively producing a specific olefin is commercially very important, and recently, a lot of studies are being progressed on the chromium catalyst technology for preparing 1-hexene or 1-octene with high selectivity through selective ethylene oligomerization.

The existing commercial preparation methods of 1-hexene or 1-octene include the SHOP process of Shell Chemical, the Ziegler process of Chevron Philips, and the like, whereby $C_{4-20}$ alpha-olefins with a wide distribution can be produced.

As a catalyst for trimerization of ethylene, a chromium-based catalyst using a ligand of the General Formula (R1)(R2)X—Y—X(R3)(R4) has been suggested. Wherein, X is phosphorous, arsenic or antimony, Y is a linking group such as —N(R5)-, and at least one of R1, R2, R3 and R4 has a polar or electron donating substituent.

And, as a ligand that exhibits catalytic activity to 1-hexene under catalytic conditions, studies have been progressed on o-ethylphenyl)$_2$PN(Me)P(o-ethylphenyl)$_2$, which does not have a polar substituent on at least one of R1, R2, R3 and R4 (*Chem. Commun.*, 2002, 858).

However, regarding the above explained ligand containing a heteroatom of the prior art, there is continued demand for consistently continued multimerization activity and high selectivity when preparing 1-octene or 1-hexene.

SUMMARY OF THE INVENTION

The present disclosure provides a novel ligand compound, a catalyst system for olefin oligomerization comprising the same, and a method for olefin oligomerization using the same that can oligomerize olefins with high catalytic activity and selectivity, and greatly reduce the production of the by-products.

The present disclosure provides a ligand compound represented by the following Chemical Formula 1.

[Chemical Formula 1]

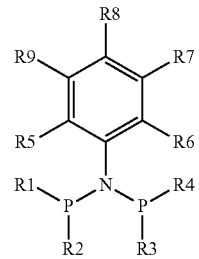

in Chemical Formula 1,

R1 to R4 are the same as or different from each other, and are each independently a C6 to C20 aryl group or a C7 to C20 alkylaryl group, R5 is a C1 to C20 alkyl group, R6 is selected from the group consisting of a C2 to C20 alkyl group optionally containing one or more heteroatoms, a C2 to C20 alkenyl group optionally containing one or more heteroatoms, a C6 to C20 aryl group, a C7 to C20 arylalkyl group, a C7 to C20 alkylaryl group, a C7 to C20 arylalkenyl group, a C7 to C20 alkenylaryl group, a C5 to C20 heteroaryl group, a C6 to C20 heteroarylalkyl group, a C6 to C20 heteroarylalkenyl group, a C3 to C20 cycloalkyl group optionally containing one or more heteroatoms and a C3 to C20 cycloalkenyl group optionally containing one or more heteroatoms, R7 to R9 are the same as or different from each other, and are each independently selected from the group consisting of hydrogen, a C1 to C20 alkyl group, a C1 to C20 alkenyl group, a C7 to C20 arylalkyl group, a C7 to C20 arylalkenyl group, a C3 to C20 cycloalkyl group, a C3 to C20 cycloalkenyl group, a C6 to C20 aryl group and a C7 to C20 alkylaryl group.

In the ligand compound, R5 may be a C2 to C20 alkyl group, or R5 and R6 may be different from each other.

And, in an exemplary embodiment of the ligand compound, when R5 is a methyl group or an isopropyl group, the C2 to C20 alkyl group optionally containing one or more heteroatoms of the R6 may be a linear alkyl group.

And, in an exemplary embodiment of the ligand compound, R7 to R9 may be hydrogen, and R1 to R4 may be phenyl groups.

Moreover, in an exemplary embodiment of the ligand compound, R5 may be a methyl group, and R6 may be selected from the group consisting of a C2 to C20 linear alkyl group, a C2 to C20 alkenyl group containing one or more heteroatoms, a C6 to C20 aryl group, a C7 to C20 arylalkyl group, a C7 to C20 alkylaryl group, a C7 to C20 arylalkenyl group, a C7 to C20 alkenylaryl group, a C5 to C20 heteroaryl group, a C6 to C20 heteroarylalkyl group, a C6 to C20 heteroarylalkenyl group, a C3 to C20 cycloalkyl group containing one or more heteroatoms and a C3 to C20 cycloalkenyl group containing one or more heteroatoms.

The present disclosure also provides a catalyst system for oligomerization, including the ligand compound, a transition metal compound and a cocatalyst, or including an organic transition metal compound wherein the ligand compound is coordinated to the transition metal.

In the catalyst system for oligomerization, the transition metal compound may include a chromium compound and the chromium compound may be at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III)acetate hydroxide.

And, in the catalyst system for oligomerization, the organic transition metal compound may be an organic chromium compound that the ligand compound is coordinated to chromium atom.

And, in the catalyst system, the cocatalyst may be at least one selected from the group consisting of the compounds represented by the following Chemical Formulae 2 to 4:

  [Chemical Formula 2]

in the Chemical Formula 2, $R_{10}$ are the same as or different from each other, and are each independently a halogen radical, a C1 to C20 hydrocarbyl radical, or a C1 to C20 hydrocarbyl radical substituted with halogen, and c is an integer of 2 or more,

  [Chemical Formula 3]

in the Chemical Formula 3,

D is aluminum or boron, $R_{11}$ are the same as or different from each other, and are each independently hydrogen, halogen, a C1 to C20 hydrocarbyl or a C1 to C20 hydrocarbyl substituted with halogen,

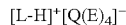  [Chemical Formula 4]

in the Chemical Formula 4,

L is neutral Lewis base, $[L-H]^+$ is Bronsted acid, Q is $Br^{3+}$ or $Al^{3+}$, and E are independently a C6 to C20 aryl group or a C1 to C20 alkyl group, unsubstituted or substituted with at least one selected from the group consisting of halogen, a C1 to C20 hydrocarbyl, an alkoxy group and a phenoxy group.

In the mean time, the present disclosure also provides a method for olefin oligomerization, including the step of multimerizing olefins in the presence of the catalyst system for olefin oligomerization.

In an exemplary embodiment of the method for olefin oligomerization, the olefin may be ethylene.

According to the method for olefin oligomerization, olefins such as ethylene can be multimerized, for example, trimerized or tetramerized to obtain alpha-olefins such as 1-hexene or 1-octene with high activity and selectivity. Further, besides the alpha-olefin desired, it is possible to reduce the content of by-products such as the solid alpha-olefin (for example, an isomer of 1-hexene having 6 carbon atoms, etc.). In an embodiment, the product produced by the method for olefin oligomerization may have a content of solid alpha-olefin of less than 1.0 wt. % based on the total weight of the product.

Advantageous Effects

In case of using the catalyst system including the ligand compound according to the present disclosure, it is possible to oligomerize ethylene with high catalytic activity and selectivity compared to existing catalyst systems, and greatly reduce the amount of the six carbon isomers (e.g., hexene isomer), which is a by-product.

DETAILED DESCRIPTION OF THE EMBODIMENTS

Hereinafter, the present disclosure will be described in more detail in order to facilitate understanding of the present invention. It should be understood that the terms and words used in the present specification and claims should not be construed as limited to general and dictionary meanings, but interpreted based on the meanings and concepts corresponding to technical aspects of the present disclosure based on the principle that the inventor is allowed to properly define the terms to describe its invention in the best way.

The terms used in this specification are just for explaining exemplary embodiments and it is not intended to restrict the present disclosure. The singular expression may include the plural expression unless it is differently expressed contextually.

It should be understood that the terms "include", "equip", "have", or the like are used to designate the existence of characteristics taken effect, numbers, steps, components, or combinations thereof, and do not exclude the existence or the possibility of addition of one or more different characteristics, numbers, steps, components of combinations thereof beforehand.

In the present specification, 'catalyst system' or 'catalyst composition' means what can be obtained as the catalyst composition having activity by mixing 3 components including a source of transition metal (for example, a transition metal compound such as an organic chromium compound), a ligand compound, and a cocatalyst, or alternatively 2 components of an organic chromium compound that the ligand compound is coordinated to the transition metal and a cocatalyst, at the same time or in an arbitrary order. Said 3 components or 2 components of the catalyst system may be mixed in the presence or absence of a proper solvent and a monomer, and the terms may be used interchangeably.

In the present specification, hydrocarbyl means all compounds consisting only of carbon and hydrogen, and includes, for example, an alkyl group, an aryl group, an alkenyl group, a cycloalkyl group and the like. In the use of the term hydrocarbyl, it may mean both linear and branched chain, and both unsubstituted and substituted unless it is especially mentioned. For example, a C1 to C20 alkyl group may include a methyl group, an ethyl group, a propyl group, an isopropyl group, a butyl group, an isobutyl group, a pentyl group, an isopentyl group and a neopentyl group, and a C6 to C20 aryl group may include a phenyl group, a naphthyl group and an anthracenyl group, but is not limited thereto.

An alkylaryl group means an aryl group having at least one alkyl group as a substituent, and an arylalkyl group means an alkyl group having at least one aryl group as a substituent.

In the present specification, a hetero atom may mean N, O, S, or P, and a heteroaryl group may mean that any one of the carbons of the aromatic ring, such as a pyridyl group, is substituted with a hetero atom. The same applies to the cases of a heteroarylalkyl group, a heteroalkylaryl group, a heteroalkenylaryl group, and the like.

Ligand Compound

According to the present disclosure, the ligand compound which is coordinated with a transition metal in the catalyst system for olefin oligomerization to obtain a high selectivity for alpha-olefin, a small amount of by-products, and a high activity of the catalyst system is provided.

According to one embodiment of present disclosure, the ligand compound is represented by the following Chemical Formula 1.

[Chemical Formula 1]

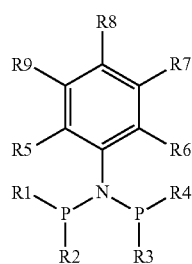

in Chemical Formula 1,

R1 to R4 are the same as or different from each other, and are each independently a C6 to C20 aryl group or a C7 to C20 alkylaryl group, R5 is a C1 to C20 alkyl group, R6 is selected from the group consisting of a C2 to C20 alkyl group optionally containing one or more heteroatoms, a C2 to C20 alkenyl group optionally containing one or more heteroatoms, a C6 to C20 aryl group, a C7 to C20 arylalkyl group, a C7 to C20 alkylaryl group, a C7 to C20 arylalkenyl group, a C7 to C20 alkenylaryl group, a C5 to C20 heteroaryl group, a C6 to C20 heteroarylalkyl group, a C6 to C20 heteroarylalkenyl group, a C3 to C20 cycloalkyl group optionally containing one or more heteroatoms and a C3 to C20 cycloalkenyl group optionally containing one or more heteroatoms, R7 to R9 are the same as or different from each other, and are each independently selected from the group consisting of hydrogen, a C1 to C20 alkyl group, a C1 to C20 alkenyl group, a C7 to C20 arylalkyl group, a C7 to C20 arylalkenyl group, a C3 to C20 cycloalkyl group, a C3 to C20 cycloalkenyl group, a C6 to C20 aryl group and a C7 to C20 alkylaryl group.

As described above, the ligand compound represented by Chemical Formula 1 may be, for example, a compound that the 2-position and 6-position carbons of the aniline compound are substituted with the R5 and R6, and the group substituted for the 2-position and 6-position carbons (R5 and R6, respectively) can change the properties of the ligand compound and the catalyst system for oligomerization including the same.

Particularly, when an alkyl group having 2 or more carbon atoms, for example, a C2 to C20 alkyl group, is substituted for the 2-position carbon (R5), or a methyl group is substituted for the 2-position carbon (R5), a substituent having a structure different from that of the 2-position carbon may be bonded to the 6-position carbon (R6).

In an embodiment of the ligand compound, when R5 is a methyl group or an isopropyl group, R6 may be a C2 to C20 linear alkyl group optionally containing one or more heteroatoms, or various asymmetric substituents as described above (i.e., substituents having a structure different from that of R5), more preferably the C2 to C20 linear alkyl group, a substituent containing one or more heteroatoms, or a substituent containing one or more aromatic groups.

In an embodiment of the ligand compound, when R5 is a methyl group, R6 may be selected from the group consisting of a C2 to C20, or C2 to C3 linear alkyl group optionally containing one or more heteroatoms, a C2 to C20, or C2 to C3 alkenyl group containing one or more heteroatoms, a C6 to C20 aryl group, a C7 to C20 arylalkyl group, a C7 to C20 alkylaryl group, a C7 to C20 arylalkenyl group, a C7 to C20 alkenylaryl group, a C5 to C20 heteroaryl group, a C6 to C20 heteroarylalkyl group, a C6 to C20 heteroarylalkenyl group, a C3 to C20 cycloalkyl group containing one or more heteroatoms and a C3 to C20 cycloalkenyl group containing one or more heteroatoms.

As described above, in the ligand compound represented by the Chemical Formula 1, both of R5 and R6 may not be methyl groups, or the ligand compound may have an asymmetric substituent structure that R5 and R6 are different from each other. In a more suitable example, the ligand compound may be a linear alkyl group having at least 2 carbon atoms, or a substituent containing at least one heteroatom or aromatic group.

Due to the structural features of the substituent of the aniline group, the catalyst system containing the ligand compound can easily react with PNP-Cr according to various conditions such as electronic and steric environment around the transition metal to exhibit not only high oligomerization reaction activity but also a high selectivity for 1-hexene, 1-octene and the like. Further, it is possible to greatly reduce the production of by-products of solid alpha-olefin form such as 1-hexene isomers which have a large effect on the product even in a small amount in the oligomerization. Additionally, due to the increase of 1-hexene and the decrease of the by-products, the separation of these may be unnecessary, and this can also bring an energy saving effect.

In the mean time, in the ligand compound represented by Chemical Formula 1, R1 to R4 and R7 to R9 may be various substituents as described above, but in a more specific example, R7 to R9 may be hydrogen and R1 to R4 may be phenyl groups.

Also, the ligand compound may be synthesized by the following Reaction Formula 1, but is not limited thereto.

[Reaction Formula 1]

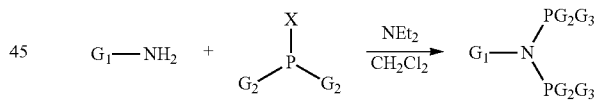

In Reaction Formula 1, G1 may be a phenyl group having R5 to R9 of the Chemical Formula 1, G2 and G3 may be respectively R1 to R4 of Chemical Formula 1, and X may be halogen.

The above Reaction Formula 1 is a general reaction formula for synthesizing the ligand compound represented by the Chemical Formula 1, and may be a reaction that amine and phosphine react to form a diphosphinoamine. In other words, it may be a reaction that the amine makes the departure of the leaving group represented by X of the phosphine as a nucleophile and is substituted for. And, the X is not particularly limited as long as it is a functional group which is easily released and is stable after being released, for example, Cl, Br, or I as halogen.

Catalyst System for Oligomerization

According to another exemplary embodiment of the present disclosure, a catalyst system for oligomerization including the ligand compound, a transition metal compound and a cocatalyst, or including an organic transition metal compound wherein the ligand compound is coordinated to the transition metal may be provided.

As used herein, the term 'oligomerization' means polymerization of a small number of olefins. For example, oligomerization collectively refers to multimerization, including trimerization or tetramerization, according to the repeating number of olefins to be polymerized. In the present disclosure, particularly, the oligomerization refers to selective preparation of 1-hexene and 1-octene, which are main comonomers of LLDPE, from ethylene.

This selective olefin oligomerization reaction is closely related to the catalyst system used. The catalyst system used in the olefin oligomerization reaction includes a transition metal compound serving as a main catalyst, a ligand compound and a cocatalyst. And, the structure of the active catalyst species can be changed according to the chemical structure of the ligand compound, thereby olefin selectivity, the activity, or the amount of by-products produced may vary.

The transition metal compound of the catalyst system for oligomerization according to the exemplary embodiment of the present disclosure serves as a main catalyst. The ligand compound may be in the form of an organic transition metal compound coordinated to a transition metal, or may be in the form of a catalyst composition present in a mixed state with the ligand compound. In the example of the organic transition metal compound, phosphorus (P) in the diphosphinoamine group of the ligand compound may be an active site, which may be coordinated while receiving electrons from the transition metal.

In an exemplary embodiment, the transition metal compound represented by $MX_3$ and the ligand compound represented by the Chemical Formula 1 may have a form of the organic transition metal compound by coordinate bonding in the form of the following Chemical Formula 1-1:

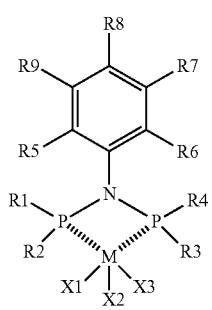

[Chemical Formula 1-1]

In the Chemical Formula 1-1, R1 to R9 are the same as in Chemical Formula 1, M may be a transition metal, preferably Cr, X1 to X3 may be each independently H, F, Cl, Br, I, or an alkyl group, an alkenyl group, an arylalkyl group, a heteroalkyl group, a heteroalkenyl group, or a heteroarylalkyl group having 1 to 6 carbon atoms, or halogen.

Specifically, the organic transition metal compound may be an organic chromium compound that the ligand compound is coordinated to chromium atom. For the chromium compound (that is, the chromium compound coordinated to the ligand compound) for forming the organic chromium compound, for example, at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III) hexafluoro-2,4-pentanedionate, and chromium(III)acetate hydroxide may be used.

The cocatalyst may be an organic metal compound containing the Group 13 metal, and is not particularly limited as long as it may be generally used in olefin oligomerization in the presence of a catalyst of a transition metal compound. Specifically, the cocatalyst may be at least one selected from the group consisting of the compounds represented by the following Chemical Formulae 2 to 4.

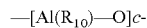—[Al(R$_{10}$)—O]$c$-   [Chemical Formula 2]

in the Chemical Formula 2, $R_{10}$ are the same as or different from each other, and are each independently a halogen radical, a C1 to C20 hydrocarbyl radical, or a C1 to C20 hydrocarbyl radical substituted with halogen, and c is an integer of 2 or more,

D(R$_{11}$)$_3$   [Chemical Formula 3]

in the Chemical Formula 3,

D is aluminum or boron, $R_{11}$ are the same as or different from each other, and are each independently hydrogen, halogen, a C1 to C20 hydrocarbyl or a C1 to C20 hydrocarbyl substituted with halogen,

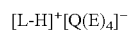[L-H]$^+$[Q(E)$_4$]$^-$   [Chemical Formula 4]

in the Chemical Formula 4,

L is neutral Lewis base, [L-H]$^+$ is Bronsted acid, Q is Br$^{3+}$ or Al$^{3+}$, and E are independently a C6 to C20 aryl group or a C1 to C20 alkyl group, unsubstituted or substituted with at least one selected from the group consisting of halogen, a C1 to C20 hydrocarbyl, an alkoxy group and a phenoxy group.

The compound represented by Chemical Formula 2 may be modified methyl aluminoxane (MMAO), methyl aluminoxane (MAO), ethyl aluminoxane, isobutyl aluminoxane, butyl aluminoxane, and the like.

The compound represented by Chemical Formula 3 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and the like.

The compound represented by Chemical Formula 4 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, triethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)

aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra(p-trifluoromethylphenyl)borate, triphenylcarbonium tetrapentafluorophenylborate, and the like.

In the catalyst system for oligomerization of the exemplary embodiment, the aluminoxane-based compound, more preferably methyl aluminoxane (MAO) or modified methyl aluminoxane (MMAO) may be used as the cocatalyst.

To increase the selectivity to linear alpha olefins and the multimerization reaction activity of the catalyst system for oligomerization, the mole ratio of the ligand compound:the transition metal compound:the cocatalyst may be controlled to be about 0.5:1:1 to about 10:1:10,000, preferably about 0.5:1:100 to about 5:1:3,000. But the catalyst system for oligomerization according to the present disclosure is not limited thereto.

In the catalyst system for oligomerization including the ligand compound represented by the Chemical Formula 1, the transition metal compound and the cocatalyst, the three components of the catalyst system may be mixed at the same time or in an arbitrary order in the presence of a proper solvent and in the presence or absence of a monomer to obtain an active catalyst. The proper solvent may be heptane, toluene, cyclohexane, methylcyclohexane, 1-hexene, diethylether, tetrahydrofuran, acetonitrile, dichloromethane, chloroform, chlorobenzene, methanol, acetone, and the like, but is not limited thereto.

Method for Olefin Oligomerization

According to another embodiment of the present disclosure, a method for olefin oligomerization, including the step of multimerizing olefins in the presence of the catalyst system for oligomerization is provided. In this method, the activity of the reaction and the selectivity may be improved by using the catalyst system for olefin oligomerization described above. In addition, the content of by-products produced as a result of oligomerization may be greatly reduced. At this time, the olefin may include ethylene.

The method for oligomerization of the present disclosure may be carried out by applying the catalyst system for oligomerization and a common device and contact technology. The oligomerization may be carried out by a homogeneous liquid phase reaction in the presence or absence of an inert solvent, by a slurry reaction using the catalyst system that is partially or not totally dissolved, by a two-phase liquid/liquid reaction, or by a bulk reaction or a gas phase reaction in which the product olefin acts as a main medium, and the homogeneous liquid phase reaction may be preferable.

The olefin oligomerization reaction may be carried out in the presence of an inert solvent that doesn't react with the catalyst compound and the activator. The proper inert solvent may be benzene, toluene, xylene, cumene, heptane, cyclohexane, methylcyclohexane, methylcyclopentane, hexane, pentane, butane, isobutene, and the like, but is not limited thereto. At this time, the solvent may be used after removing a small amount of water or air acting as a catalyst poison by treating with a small amount of alkylaluminum.

The olefin oligomerization reaction may be carried out at a temperature of about 5° C. to about 200° C., preferably about 30° C. to about 150° C. The olefin oligomerization reaction may be carried out at a pressure of about 1 bar to about 300 bar, preferably about 2 bar to about 150 bar.

The range of the temperature and pressure may be an optimal condition for olefin multimerization reaction. When the olefin is multimerized in the range of the temperature and pressure above, the selectivity to the desired alpha-olefin may be excellent, the amount of by-products may be reduced, the efficiency of the process operation may be increased, and the cost may be reduced.

According to one embodiment of the present disclosure, the catalyst system using the compound represented by Chemical Formula 1 as a ligand may have improved activity compared with the conventional oligomerization catalyst system. Therefore, when ethylene is oligomerized using the catalyst system, 1-hexene and 1-octene may be selectively synthesized, and the amount of the 1-hexene isomer may be greatly reduced, which can be confirmed in the following examples.

EXAMPLES

Hereinafter, embodiments of the present invention are described in detail so that those skilled in the art are able to easily perform. But the present disclosure may be embodied in various forms, and the scope of the present disclosure is not limited to the examples provided herein.

<Synthesis of the Ligand Compound>

All the reactions were carried out under argon using Schlenk technique or a glovebox. The synthesized ligands were analyzed by $^1$H (500 MHz) and $^{31}$P (202 MHz) NMR spectra using a Varian 500 MHz spectrometer. The shifts were expressed in ppm as a downfield from TMS with a residual solvent peak as a reference. The phosphorous probes were calibrated with aqueous $H_3PO_4$.

Synthesis Example 1

Under argon, 2-ethyl-6-methylaniline (10 mmol) and triethylamine (3 equiv. to amine) were dissolved in dichloromethane (80 mL). While the flask was immersed in a water bath, chlorodiphenylphosphine (20 mmol) was slowly introduced, and the mixture was stirred overnight. After the solvent was removed under vacuum, another solvent (diethyl ether, tetrahydrofuran or hexane) was introduced, the mixture was sufficiently stirred, and triethylammonium chloride salt was removed by an air-free glass filter. The solvent was removed in the filtrate to obtain a product.

Synthesis Example 2

The ligand compound was prepared by the same method as Synthesis Example 1, except using 2,6-diethylaniline instead of the 2-ethyl-6-methylaniline used in Synthesis Example 1.

Synthesis Example 3

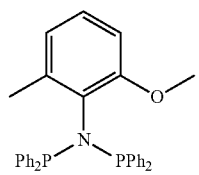

The ligand compound was prepared by the same method as Synthesis Example 1, except using 2-methoxy-6-methylaniline instead of the 2-ethyl-6-methylaniline used in Synthesis Example 1.

Synthesis Example 4

The ligand compound was prepared by the same method as Synthesis Example 1, except using 2,4-dimethyl-6-phenylaniline instead of the 2-ethyl-6-methylaniline used in Synthesis Example 1.

Comparative Synthesis Example 1

The ligand compound was prepared by the same method as Synthesis Example 1, except using 2,6-dimethylaniline instead of the 2-ethyl-6-methylaniline used in Synthesis Example 1.

Comparative Synthesis Example 2

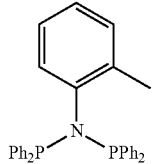

The ligand compound was prepared by the same method as Synthesis Example 1, except using 2-methylaniline instead of the 2-ethyl-6-methylaniline used in Synthesis Example 1.

Preparation of Alpha-Olefin Oligomers

Example 1

(Step 1)
Under argon gas, $Cr(acac)_3$ (17.5 mg, 0.05 mmol) and the ligand compound prepared in the Synthesis Example 1 (1.1 eq. to Cr) were introduced in a flask, methylcyclohexane (100 mL) was added, and the mixture was stirred to prepare a 0.5 mM (based on Cr) solution.

(Step 2)
A 600 mL Parr reactor was prepared, vacuum was applied at 120° C. for 2 hours, and then, the inside was replaced with argon, and the temperature was decreased to 45° C. And, 140 g of methylcyclohexane and 1.6 ml of MMAO (8.6 wt %, isoheptane solution) were introduced, and 5 mL of the 0.5 mM solution (2.5 umol) was introduced in the reactor. A valve of an ethylene line adjusted to 60 bar was opened to fill the inside of the reactor with ethylene, followed by stirring at 500 rpm for 15 minutes. The valve of an ethylene line was closed, the reactor was cooled down to 0° C. with a dry ice/acetone bath, and then, non-reacted ethylene was slowly vented, and 1 ml of nonane (GC internal standard) was introduced. And then, a portion of the liquid part of the reactor was taken and quenched with water, and the organic part was filtered with a PTFE syringe filter to be analyzed by GC.

(Step 3)
To the remaining reaction solution, 400 mL of ethanol/HCl (10 vol %) was added, and the mixture was stirred and filtered to obtain polymer. The obtained polymer was dried overnight in a 60° C. vacuum oven, and weighed.

Example 2

Oligomerization, GC analysis and weighing of the obtained polymer were carried out in the same manner as in Example 1, except using the ligand compound prepared in Synthesis Example 2 instead of the ligand compound prepared in Synthesis Example 1.

Example 3

Oligomerization, GC analysis and weighing of the obtained polymer were carried out in the same manner as in Example 1, except using the ligand compound prepared in Synthesis Example 3 instead of the ligand compound prepared in Synthesis Example 1.

Example 4

Oligomerization, GC analysis and weighing of the obtained polymer were carried out in the same manner as in Example 1, except using the ligand compound prepared in Synthesis Example 4 instead of the ligand compound prepared in Synthesis Example 1.

Comparative Example 1

Oligomerization, GC analysis and weighing of the obtained polymer were carried out in the same manner as in Example 1, except using the ligand compound prepared in Comparative Synthesis Example 1 instead of the ligand compound prepared in Synthesis Example 1.

Comparative Example 2

Oligomerization, GC analysis and weighing of the obtained polymer were carried out in the same manner as in Example 1, except using the ligand compound prepared in Comparative Synthesis Example 2 instead of the ligand compound prepared in Synthesis Example 1.

The results of Examples 1 to 4 and Comparative Examples 1 and 2 are shown in the following Table 1.

TABLE 1

|  | Ligand compound | Activity ton/molCr/hr | 1-hexene wt % | 1-octene wt % | 1-hexene + 1-octene wt % | $C_6$ isomers wt % |
| --- | --- | --- | --- | --- | --- | --- |
| Example 1 | Synthesis Example 1 | 161 | 49.5 | 40.5 | 90.0 | 1.5 |
| Example 2 | Synthesis Example 2 | 165 | 50.5 | 39.1 | 89.6 | 1.4 |
| Example 3 | Synthesis | 102 | 22.7 | 59.7 | 82.4 | 6.6 |

TABLE 1-continued

|  | Ligand compound | Activity ton/molCr/hr | 1-hexene wt % | 1-octene wt % | 1-hexene + 1-octene wt % | $C_6$ isomers wt % |
|---|---|---|---|---|---|---|
| Example 4 | Example 3 Synthesis Example 4 | 127 | 29.5 | 57.1 | 86.6 | 3.3 |
| Comparative Example 1 | Comparative Synthesis Example 1 | 161 | 37.4 | 51.1 | 88.5 | 1.8 |
| Comparative Example 2 | Comparative Synthesis Example 2 | 62 | 16.7 | 60.9 | 77.6 | 9.5 |

As shown in Table 1, it was confirmed that using the ligand compounds of Synthesis Examples 1 and 2 produced a smaller amount of by-products such as $C_6$ isomers, and exhibited a higher HAO selectivity than the case using the ligand compounds of Comparative Synthesis Example 1.

Further, even in Example 3 using a hetero atom-substituted ligand compound (Synthesis Example 3), it was confirmed that there was no problem in using the catalyst system with the group containing the hetero atom for the oligomerization reaction. In addition, it was confirmed that Example 4 using an aryl group-substituted ligand compound (Synthesis Example 4) was also very useful for the oligomerization reaction.

While the preferred examples of the present invention have been shown and described in detail, it should be understood that various substitutions, modifications and variations may be made by those skilled in the art without departing from the spirit or scope of the invention. Accordingly, all such modifications and variations are included in the scope of the invention as defined by the following claims.

The invention claimed is:

1. A ligand compound represented by the following Chemical Formula 1:

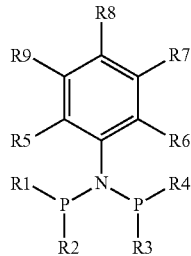

[Chemical Formula 1]

in Chemical Formula 1,
R1 to R4 are the same as or different from each other, and are each independently a C6 to C20 aryl group or a C7 to C20 alkylaryl group,
R5 is a C1 to C20 alkyl group,
R6 is selected from the group consisting of a C2 to C20 linear alkyl group, and
R7 to R9 are the same as or different from each other, and are each independently selected from the group consisting of hydrogen, a C1 to C20 alkyl group, a C1 to C20 alkenyl group, a C7 to C20 arylalkyl group, a C7 to C20 arylalkenyl group, a C3 to C20 cycloalkyl group, a C3 to C20 cycloalkenyl group, a C6 to C20 aryl group and a C7 to C20 alkylaryl group.

2. The ligand compound of claim 1, wherein R5 is a C2 to C20 alkyl group, or R5 and R6 are different from each other.

3. The ligand compound of claim 1, wherein R5 is a methyl group, ethyl or an isopropyl group.

4. The ligand compound of claim 1, wherein R7 to R9 in Chemical Formula 1 are hydrogen.

5. The ligand compound of claim 1, wherein R1 to R4 in Chemical Formula 1 are phenyl groups.

6. The ligand compound of claim 1, wherein R5 is a methyl group.

7. A catalyst system for oligomerization, comprising:
the ligand compound according to claim 1, a transition metal compound and a cocatalyst, or
the ligand compound according to claim 1, an organic transition metal compound wherein the ligand compound is coordinated to the transition metal, and a cocatalyst.

8. The catalyst system for oligomerization of claim 7, wherein the transition metal compound comprises a chromium compound and the chromium compound is at least one selected from the group consisting of chromium(III) acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III)acetate hydroxide.

9. The catalyst system for oligomerization of claim 7, wherein the organic transition metal compound is an organic chromium compound, and the ligand compound is coordinated to the chromium atom.

10. The catalyst system for oligomerization of claim 7, wherein the cocatalyst is at least one selected from the group consisting of the compounds represented by the following Chemical Formulae 2 to 4:

—[Al(R$_{10}$)—O]c-   [Chemical Formula 2]

in the Chemical Formula 2, R$_{10}$ are the same as or different from each other, and are each independently a halogen radical, a C1 to C20 hydrocarbyl radical, or a C1 to C20 hydrocarbyl radical substituted with halogen, and c is an integer of 2 or more, D(R$_{11}$)$_3$   [Chemical Formula 3]

in the Chemical Formula 3,
D is aluminum or boron, R$_{11}$ are the same as or different from each other, and are each independently hydrogen, halogen, a C1 to C20 hydrocarbyl or a C1 to C20 hydrocarbyl substituted with halogen,

[L-H]$^+$[Q(E)$_4$]$^-$   [Chemical Formula 4]

in the Chemical Formula 4,

L is neutral Lewis base, $[L-H]^+$ is Bronsted acid, Q is $Br^{3+}$ or $Al^{3+}$, and E are independently a C6 to C20 aryl group or a C1 to C20 alkyl group, unsubstituted or substituted with at least one selected from the group consisting of halogen, a C1 to C20 hydrocarbyl, an alkoxy group and a phenoxy group.

11. A method for olefin oligomerization, comprising the step of oligomerizing olefins in the presence of the catalyst system for oligomerization of claim 7.

12. The method for olefin oligomerization according to claim 11, wherein the olefins comprise ethylene.

* * * * *